United States Patent [19]

Kutney et al.

[11] Patent Number: 5,770,749

[45] Date of Patent: Jun. 23, 1998

[54] PROCESS OF ISOLATING A PHYTOSTEROL COMPOSITION FROM PULPING SOAP

[75] Inventors: James P. Kutney, Vancouver; Egon Novak, Richmond; Peter J. Jones, Montreal, all of Canada

[73] Assignee: The University of British Columbia - University Maison Office (Industrial), Vancouver, Canada

[21] Appl. No.: 706,354

[22] Filed: Aug. 30, 1996

Related U.S. Application Data

[63] Continuation of Ser. No. 314,945, Sep. 29, 1994, abandoned.

[51] Int. Cl.$^6$ ...................................................... C07J 75/00
[52] U.S. Cl. .............................................................. 552/545
[58] Field of Search ............................................... 552/545

[56] References Cited

U.S. PATENT DOCUMENTS

| 4,044,031 | 8/1977 | Johansson et al. | 260/397.25 |
|---|---|---|---|
| 4,265,824 | 5/1981 | Koskenniska et al. | 260/397.25 |
| 4,279,827 | 7/1981 | Ukkonen et al. | 260/397.25 |

*Primary Examiner*—Kimberly J. Prior
*Attorney, Agent, or Firm*—Susan M. Ben-Oliel

[57] ABSTRACT

The invention is drawn to a process for isolating and purifying a phytosterol composition from a pulping soap by first extracting a creamy precipitate from the pulping soap using a solvent mixture of water, ketone, and hydrocarbon, and then purifying the cremy precipitate to form the phytosterol composition. The invention also includes the phytosterol composition formed by this method.

6 Claims, 13 Drawing Sheets

FIGURE 4

| INDEX | TIME (MIN.) | AREA V*s | AREA % | BASELINE V | HEIGHT V | TRUE % |
|---|---|---|---|---|---|---|
| 73 | 34.650 | 0.039 | 0.051 | 0.016 | 0.005 | 0.890674 |
| 74 | 35.267 | 0.029 | 0.037 | 0.016 | 0.004 | 0.646175 |
| 75 | 36.629 | 0.087 | 0.114 | 0.017 | 0.007 | 1.990919 |
| 76 | 36.808 | 0.004 | 0.005 | 0.019 | 0.001 | 0.087321 |
| 77 | 37.054 | 0.093 | 0.121 | 0.017 | 0.011 | 2.113168 |
| 78 | 37.354 | 0.16 | 0.208 | 0.017 | 0.014 | 3.632553 |
| 79 | 37.492 | 0.018 | 0.024 | 0.022 | 0.003 | 0.419141 |
| 80 | 37.879 | 0.094 | 0.123 | 0.017 | 0.01 | 2.148096 |
| 81 | 38.688 | 0.615 | 0.789 | 0.017 | 0.057 | 13.93643 |
| 82 | 39.675 | 0.24 | 0.311 | 0.017 | 0.017 | 5.431366 |
| 83 | 39.908 | 0.021 | 0.027 | 0.021 | 0.003 | 0.471533 |
| 84 | 40.208 | 0.377 | 0.49 | 0.017 | 0.039 | 8.557457 |
| 85 | 40.675 | 0.269 | 0.35 | 0.017 | 0.02 | 6.112469 |
| 86 | 41.154 | 0.33 | 0.428 | 0.017 | 0.03 | 7.474677 |
| 87 | 42.229 | 1.862 | 2.416 | 0.017 | 0.124 | 42.1935 |
| 88 | 42.625 | 0.088 | 0.114 | 0.017 | 0.005 | 1.990919 |
| 89 | 43.646 | 0.039 | 0.05 | 0.017 | 0.004 | 0.87321 |
| 90 | 46.742 | 0.045 | 0.059 | 0.017 | 0.004 | 1.030388 |
| 34.65 | | | 5.726 | | 0.02168 | 73 |
| 35.26667 | | | | | 0.02064 | 74 |
| 36.62917 | | | | | 0.02328 | 75 |
| 36.80833 | | | | | 0.02011 | 76 |
| 37.05416 | | | | | 0.02706 | 77 |

FIGURE 7

| INDEX | TIME (MIN.) | AREA V*s | AREA % | BASELINE V | HEIGHT V |
|---|---|---|---|---|---|
| 1 | 4.012 | 0.078 | 3.224 | 0.011 | 0.033 |
| 2 | 4.496 | 0.161 | 6.649 | 0.011 | 0.017 |
| 3 | 4.775 | 0.007 | 0.269 | 0.018 | 0.004 |
| 4 | 32.117 | 0.05 | 2.077 | 0.009 | 0.011 |
| 5 | 32.433 | 0.093 | 3.858 | 0.009 | 0.009 |
| 6 | 40.217 | 0.347 | 14.328 | 0.01 | 0.041 |
| 7 | 41.879 | 0.389 | 16.064 | 0.01 | 0.038 |
| 8 | 44.058 | 1.297 | 53.532 | 0.01 | 0.074 |

PROCESS OF ISOLATING A PHYTOSTEROL COMPOSITION FROM PULPING SOAP

This application is a continuation of application Ser. No. 80/314,945 filed on Sept. 29, 1994 now abandoned.

FIELD OF THE INVENTION

This invention relates to the preparation and purification of sterol compositions item pulping soaps, to the actual compositions per se and to the use of these compositions and derivatives thereof as agents to prevent or treat primary and secondary dyslipidemias.

BACKGROUND OF THE INVENTION

The direct cause of heart attack and angina is a degenerative process known as atherosclerosis. Atherosclerosis results from a number of integrated inherited (genetic) and environmental factors. The interplay of these factors, of which diet in our civilization appears to be the most important, leads to the development of atherosclerosis. Growth of cholesterol filled atherosclerotic plaques ultimately cuts of blood supply to the heart muscle, or alternately to brain or legs, depending on the location of the plaque in the arterial tree.

One of the major risk factors for atherosclerosis that is potentially modifiable is the level of blood cholesterol. A number of well documented studies have shown that the blood cholesterol level is indeed an important predictor for the risk of heart attack and also for strokes. The relationship between blood concentration of cholesterol and risk of these disorders is continuous (spans across all levels of cholesterol) graded (the higher the level, the more likely the disease) with no apparent threshold (even by lowering so-called low levels, one can further decrease risk of the disease). For example, in people over 40 years of age, a blood cholesterol level of 7.0 mmol/L presents a risk of coronary artery disease three to four times that associated with levels below 5.0 mmol/L. The relationship becomes especially steep when the levels are above 5.2 mmol/L. For instance, the death rate among men with cholesterol of levels 8.0 mmol/L was almost six times that among men with levels of 4.0 mmol/L. These more recent findings are consistent with earlier studies.

Other large clinical trials have shown clearly that by lowering high cholesterol levels, one can reduce the risk of fatal and non-fatal myocardial infarctions, angina, changes in electrocardiograms and in coronary artery bypass surgery. The best known and the first of these trials was at Lipid Research Clinics at which Coronary Primary Prevention Trials showed that with every 1% reduction in total blood cholesterol level, there was a 2% reduction in the risk of coronary artery disease.

For any long term preventative therapy of hypercholesterolemia to be successful, it has to be commenced at a relatively early age and continue indefinitely. While a low-fat diet is the corner stone of such long term therapy, up to 60% of patients become non-compliant after six months. The difficulty in non-compliance is marked in many Western countries by a general diet which is high in fat. The poor cholesterol profile of many patients is exacerbated by the prevalence of additional risk factors for cardiovascular disease such as high blood pressure, diabetes, obesity and smoking.

Dietary modification as a therapy for atherosclerosis and other cardiovascular diseases has been refined significantly over the past 10 to 15 years. In particular, it has been recognized by researchers that plant sterols (phytosterols) are effective in lowering plasma cholesterol levels: Lees et al. *Atherosclerosis*, 28 (1977) 325–338; Kudehodkar et al., *Atherosclerosis*, 23 (1976) 239; Day. *Artery*, 18(3):125–132 (1991).

Phytosterols are sterol-like compounds synthesised in plants with no nutritional value to humans. In plants they are required for cell function in a manner similar to the way in which cholesterol is required in humans. The average Western diet contains up to 360 mg of phytosterols per day. Recently, these dietary plant sterols have received a great deal of attention because of their possible anti-cancer properties and their ability to decrease cholesterol levels when fed to a number of mammalian species, including humans.

Chemically, phytosterols closely resemble cholesterol in structure. The major phytosterols are beta-sitosterol, campesterol and stigmasterol. Others include stigmastanol (beta-sitostanol). sitostanol. desmosterol, chalinasterol, poriferasterol. clionasterol and brassicasterol. The chemical structures of beta-sitosterol, campesterol and stigmasterol are as follows:

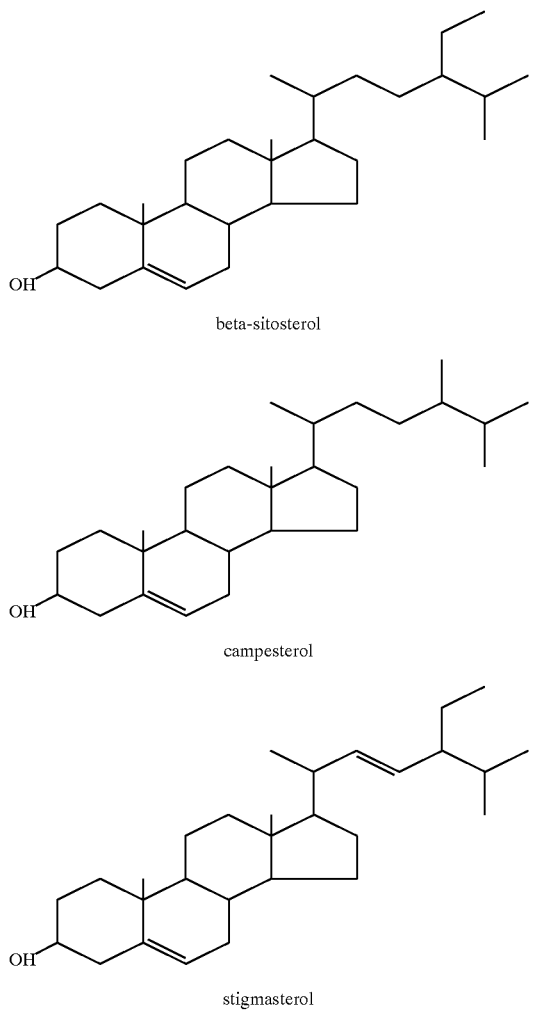

beta-sitosterol campesterol stigmasterol

The mechanism by which phytosterols lower blood cholesterol in animals is unclear, but it appears to involve the inhibition of cholesterol absorbtion from the proximum jejunum by competing with cholesterol at specific uptake sites. Research data has also suggested that some phytosterols are not absorbed at the proximal jejunum at all (sitostanol) and, when there is absorbtion (beta-sitosterol), it is in very limited quantities.

Based on these research findings, the use of phytosterols as a dietary supplement to reduce cholesterol absorbtion has been widely investigated. Lees et al., supra; Pollak, *Pharmac. Ther.*, 31 (1985) 177–208; Raicht et al., *Biochimica et Biophysica Acta*, 388 (1975) 374–384.

In Lees et al., supra, a comparison was made between the effects of siterosterol preparations from two sources, soy sterols and tall oil sterols, on plasma cholesterol. Plant sterol preparations were found to be effective in treating patients with hypercholesterolemia. Pollak, supra, is a survey paper of phytosterols and their effect on serum lipids. Raicht, supra, describes further the effect of beta-sitosterol on sterol balance and rate-limiting enzymes of sterol metabolism.

It is generally accepted that phytosterols offer a unique combination of long-term safety, efficacy, and versatility in human treatment. The ongoing challenge with respect to phytosterols is in their isolation and purification from plant sources and in determining additional sources which are cost-effective, manageable on a large-scale and which exhibit hypocholesteremic effects.

Traditionally, phytosterols have been isolated from sources such as corn oil, wheat germ oil, soya bean pitch and corn oil pitch. Similarly, tall oil pitch, which is obtained during the process of preparing paper from wood, particularly pine wood, has been used as a phytosterol source. Generally, in this process, wood chips are digested with caustic soda to produce a pulp or "soap". The soap is then distilled to remove the volatile materials leaving a "pitch" as the residue. It is from this pitch that researchers have isolated phytosterols.

There are some marked disadvantages to these traditional sources of phytosterols. The tall oil pitch is an extremely complex material comprising resins, fatty acids, oxidation products, esterified materials and phytosterols. Although the pitch is inexpensive in that it is the tailing left from various manufacturing processes, it is very difficult to recover high molecular weight sterols from it in good yields and at the high purities required for pharmaceutical uses.

U.S. Pat. No. 3,840,570 to Jullan provides a process for preparing sterols from tall oil pitch by extraction in a water-alcohol-hydrocarbon mixture followed by saponification and subsequent purification. The starting material in this process is tall oil pitch from which are extracted phytosterols and various impurities. It is recognized that, in any tall oil pitch purification process, the long-chain alcohol and acid impurities are particularly difficult to separate from the sterols (which are, themselves, high molecular weight alcohols).

Other researchers have addressed the issue of sterol purification from tall oil pitch: U.S. Pat. No. 2,835,682 to Steiner and Fritz; U.S. Pat. No. 2,715,638 to Albrecht and Herrlinger; U.S. Pat. No. 2,573,891 to Christenson. It is important to note that in each of these known purification processes, the starting material was tall oil pitch which has the recovery problems discussed above.

It is an object of the present intention to obviate or mitigate the above disadvantages.

SUMMARY OF THE INVENTION

The present invention provides a process for purifying and preparing phytosterol compositions from pulping soap which comprises extracting from the pulping soap a creamy precipitate and purifying this precipitate to form a unique phytosterol composition. More specifically, the creamy precipitate is extracted from the pulping soap using a solvent extraction procedure. The resultant composition is then purified from the creamy precipitate by crystallization.

The present invention also provides unique compositions which are effective in preventing or treating dyslipidemias and which comprise beta-sitosterol, campesterol and stigmastanol. The phytosterol compositions provided herein are significantly different from those found in plants, foods and oils. In particular, the provision of stigmastanol appears to enhance the efficacy. These compositions may additionally comprise various co-occurring compounds, which may or may not be phytosterols. In particular, these co-occurring compounds may include triterpenes, long chain alcohols and other alcohol-soluble organic compounds.

The present invention further provides the use of the compositions described herein to prevent or treat primary and secondary dyslipidemias and atherosclerosis including coronary heart disease, peripheral vascular disease and strokes in humans and animals.

The unique compositions of the present invention have exhibited excellent results in lowering total (TC) and low density lipoprotein (LDL) blood cholesterol. In addition, and quite surprisingly, the compositions of the present invention were found, in different animal species, to maintain or elevate plasma levels of high-density lipoprotein (HDL) blood cholesterol. This feature of the present invention is critically important given the fact that research has shown that, irrespective of TC levels, as the plasma HDL level decreases, the risk of atherosclerosis increases. Phytosterols isolated from tall oil pitch, soybean and other sources have not, to the knowledge of the present inventors, exhibited this unique HDL effect.

Although it is known to produce some types of phytosterols from the pitch distilled from the soap of wood chip treatments, phytosterol compositions have not heretofore been produced from the pulping soap component of the wood chip treatment process. The tall oil pitch is significantly different in composition from the pulping soap. It is believed that the surprising effect of the compositions of the present invention is due, at least partially, to the use of the pulping soap as the starting material and to the unique separation process.

BRIEF REFERENCE TO THE DRAWINGS

Various aspects of the invention will be illustrated by the following non-limiting drawings wherein:

FIG. 4 is an index of the gas-chromatography profile of FIG. 1;

FIG. 7 is an index of the gas-chromatography profile of FIG. 5;

PREFERRED EMBODIMENTS OF THE INVENTION

The process of the present invention comprises the steps of:

(A) obtaining or preparing the starting material, a plant-derived pulping soap;

(B) extracting from the soap a creamy precipitate using an appropriate solvent; and (C) purifying from the creamy precipitate a phytosterol composition.

There are numerous possible sources of the plant-derived pulping soap. Generally, in a known process (the "Kraft" process) wood chips are treated with caustic soda to produce a soap. The wood chips may be derived from any hard wood or soft wood variety of tree including, but not limited to, fir, cedar, pine, spruce, oak, hemlock and poplar. Most preferably, the chips are derived from any Pacific Northwest American or European forest variety of woods.

In the extraction phase, the soap is mixed with a ketone and water solution. A hydrocarbon solvent is used to extract the sterols. This step can be performed at temperatures generally from about 25° C. to about 150° C, but most preferably from about 50° C. to about 100° C. Most preferably, this extraction phase is continued over 15 to 24 hours.

The ketone is selected from the group having the general structure $RCOR^1$ where R and $R^1$ are alkyl groups. Preferably the alkyl groups are $C_1$–$C_6$ groups. Most preferably, the ketone is 2-propanone (acetone). The hydrocarbon may be selected from the group comprising all $C_5$–$C_{10}$ hydrocarbons. Most preferably, the hydrocarbon is hexane.

Figure 1:
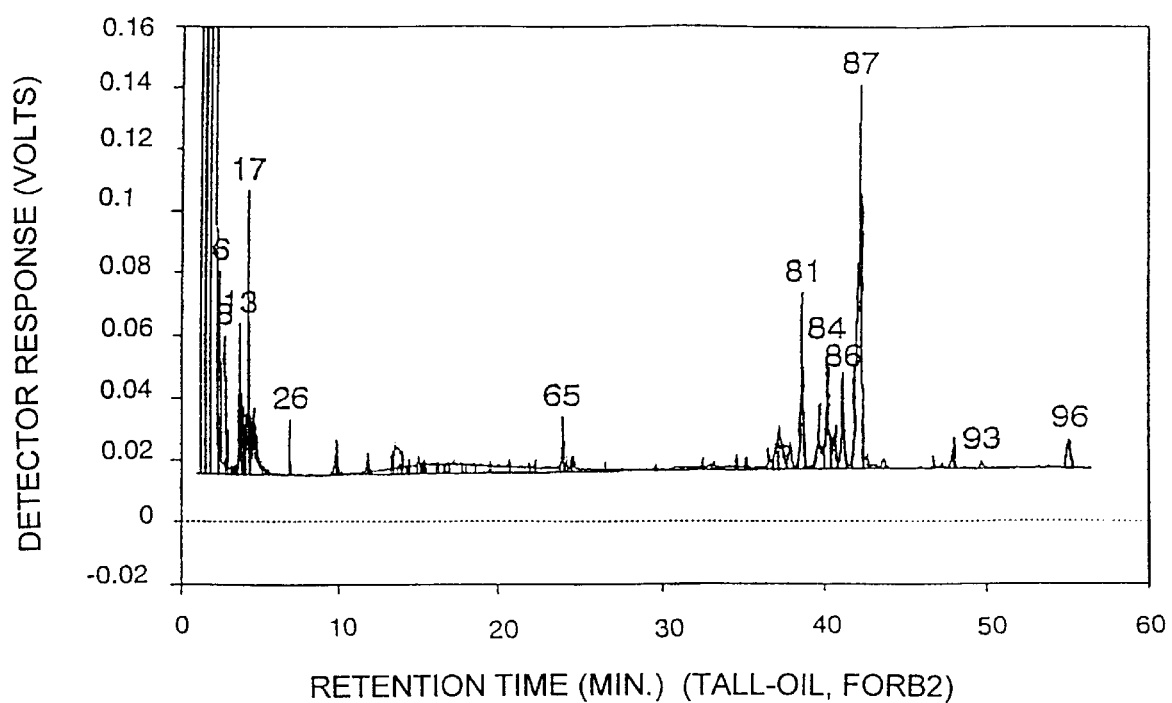
FIG. 1 is a gas-chromatography profile for one composition (hereinafter Forbes-2) within the scope of the present invention.

As depicted in FIG. 1, the product of the extraction phase is a creamy precipitate or residue from which is purified the phytosterol composition. This purification phase may be conducted by crystallization, chromatographic separation or by any other suitable procedures. Most preferably, the creamy precipitate is dissolved in alcohol, cooled slowly, then filtered and washed with cold alcohol. The residue is dried, and the resultant product is a phytosterol composition.

In a preferred form, the alcohol used in the purification phase is selected from the group having the general structures R—CHOHR, R—CH$_2$OH, and RCOH where R is a $C_1$–$C_4$ alkyl group. Most preferably, the alcohol is methanol. The cooling phase may be affected at temperatures from 10° Celsius to 0° Celsius, most preferably at 3° to 4° Celsius for 24 hours.

The phytosterol compositions resulting from the processes described herein may be incorporated directly into food supplements and vitamin formulations and into drugs for on-going and preventive treatment of atherosclerosis and its consequences, strokes, heart attacks and peripheral vascular disease. In addition, it is contemplated within one embodiment of the present invention that the phytosterol compositions described herein be provided in the form of medications with suitable adjuvants or carriers. For example, these compositions may be incorporated or prescribed concurrently with selected lipid-lowering agents, to decrease the necessary dosage, and hence the toxicity, of these latter compounds.

The phytosterol compositions of the present invention have exhibited a marked ability to modify lipoproteins, even at lower phytosterol concentrations than in known formulations. More surprisingly, however, has been the effect of these compositions on increasing plasma levels of high density lipoproteins (HDL), an effect heretofore not associated with any other tall oil-derived phytosterol composition. It is believed that this unique effect may be due to the use of pulping soaps as the starting material or the provision of stigmastanol as an element of the composition.

In a preferred form, the compositions of the present invention comprise the following ratio of phytosterols: beta-siterosterol (1); campesterol (0.2–0.4) and stigmastanol (0.2–0.5). More preferably, campesterol and stigmastanol together represent at least 50% of the total concentration of beta-sitosterol. In a most preferred form, the compositions of the present invention comprise the following ratio of phytosterols as compared to soybean-derived phytosterols:

|  | Approximate Purity (%) | Ratio of Known Phytosterols | | |
|---|---|---|---|---|
|  |  | B-Sitosterol | Campesterol | Stigmastanol |
| Soybean |  | 1 | 0.640 | 0.005 |
| Forbes-1 | 91.0 | 1 | 0.354 | 0.414 |
| Forbes-2 | 77.0 | 1 | 0.330 | 0.203 |
| Forbes-3 | 90.0 | 1 | 0.268 | 0.299 |

The composition and purity of two other extracts within the scope of the present invention are as follows:

|  | Approximate Purity (%) | Composition (%) | | |
|---|---|---|---|---|
|  |  | B-Sitosterol | Campesterol | Stigmastanol |
| Forbes-4 | 99.0 | 62.6 | 16.6 | 23.2 |
| Forbes-5 | 98.3 | 64.7 | 16.4 | 17.2 |

In every composition described herein, there may be additional compounds present which may or may not be phytosterols. In order to determine the nature of these co-occurring compounds, gas liquid chromatography analysis has been conducted on each of the most preferred compositions of the present invention.

Gas chromatography running conditions for the phytosterols were: initial temperature 80° C. which was held for 1 minute; ramp to 120° C. at 20° C. per minute, which was held for 7 minutes; ramp to 24° C. at 20° C. per minute which was held for 15 minutes; and ramp to 269° C. at 20° C. per minute which was held for 25 minutes. At the end of each run, the temperature was ramped to 320° C. and held for a minimum of 5 minutes. The injection temperature was 300° C. and the detector temperature was 320° C. The column flow rate was 1 ml per minute and the split vent flow rate was 4 ml minute. The purge vent flow rate was 4.5 ml minute. The carrier gas was helium.

The results of the gas liquid chromatography analysis for two of the most preferred compositions of the present invention are depicted in FIGS. 1–7.

Figure 2:
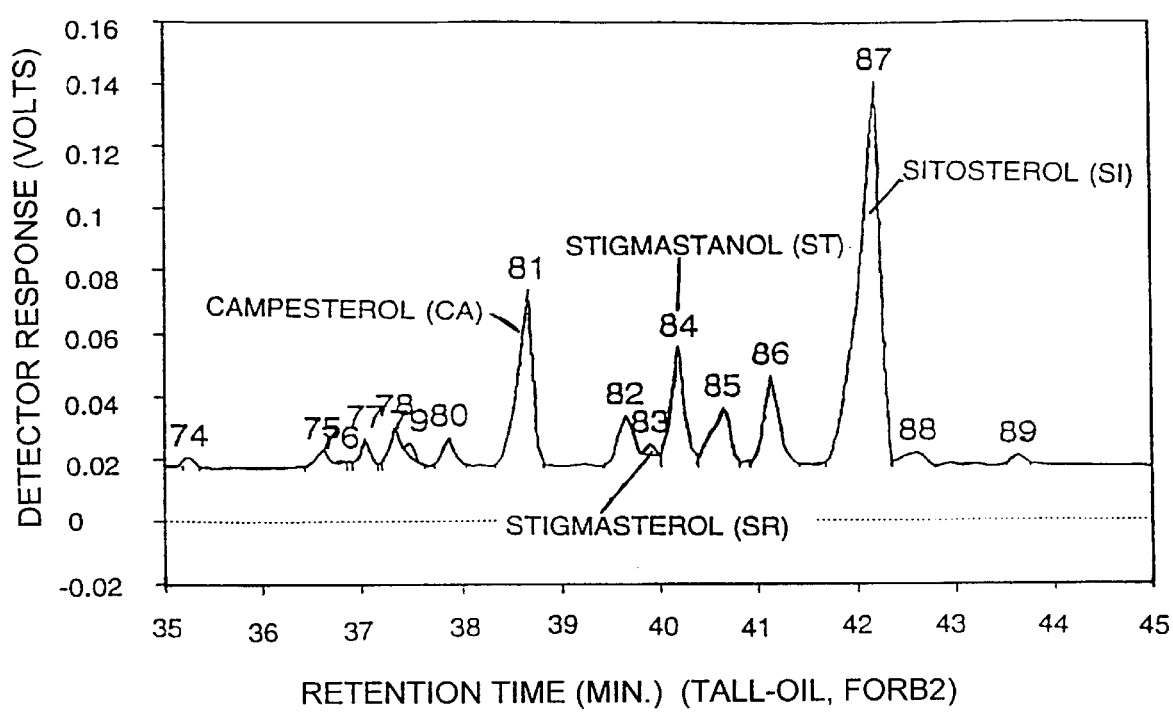
FIG. 2 is a representation of the profile in FIG. 1 from 35 to 45 minutes retention time.
Figure 3:
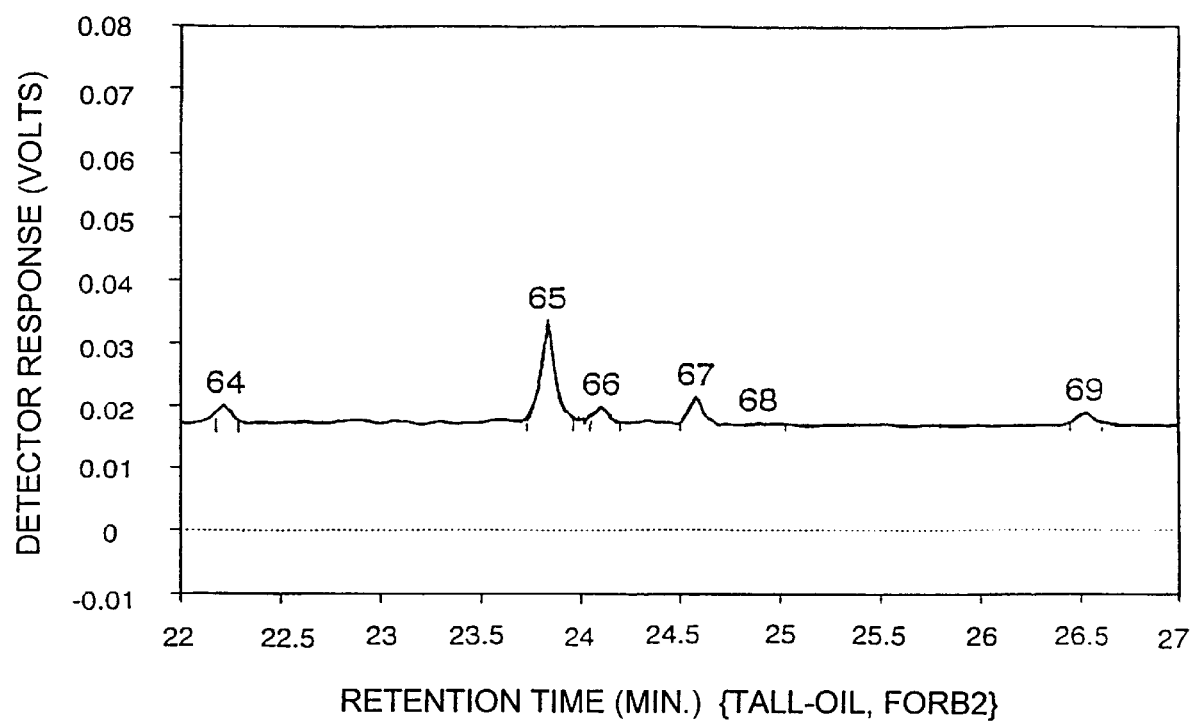
FIG. 3 is a representation of the profile in FIG. 1 from 22 to 27 minutes retention time.
Figure 5:
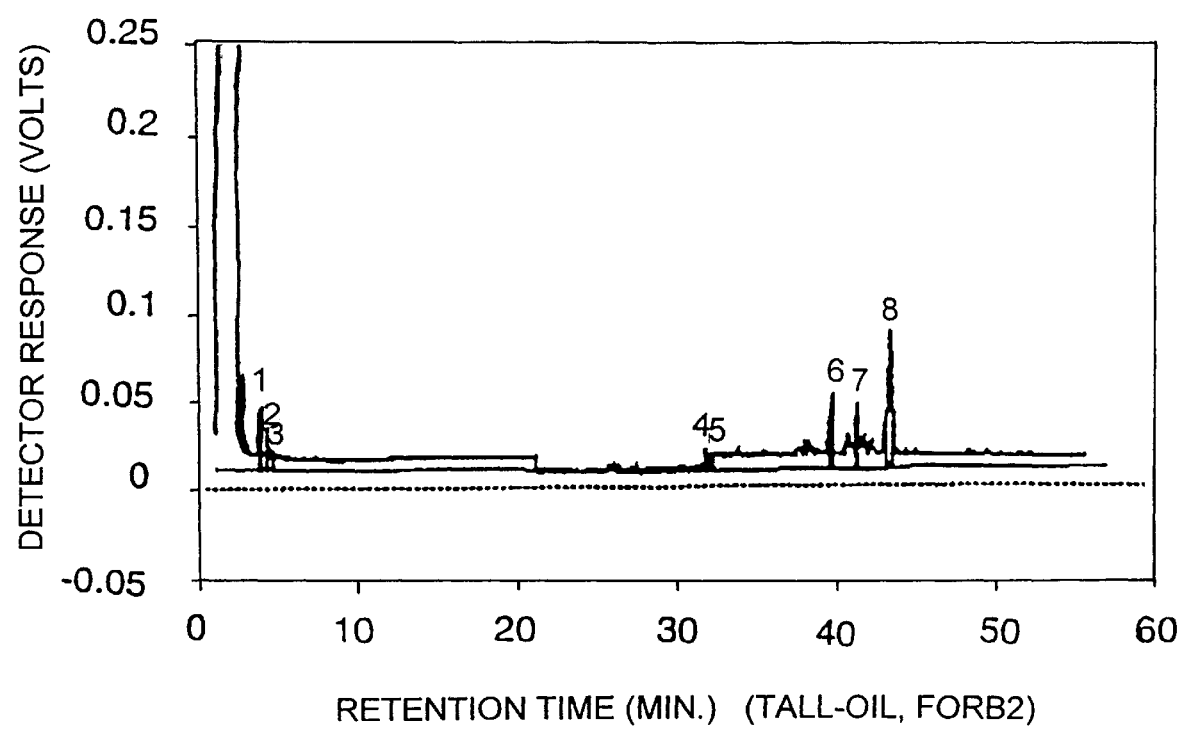
FIG. 5 is a gas-chromatography profile for another composition (hereinafter Forbes-3) within the scope of the present invention.
Figure 6:
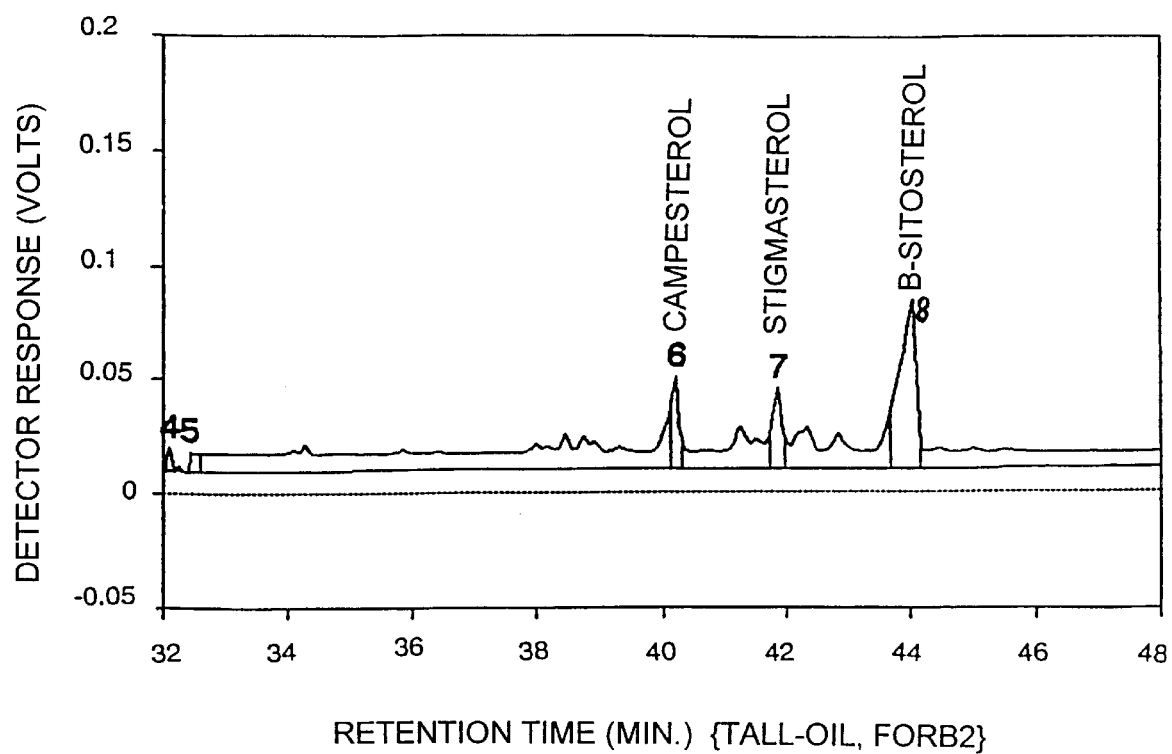
FIG. 6 is a representation of the profile in FIG. 5 from 32 to 48 minutes retention time.

With respect to the Forbes-2 composition, the known sterols appear in the 35–45 minute region in FIGS. 1 and 2. Beta-sitosterol is indicated at peak 87; campesterol is indicated at peak 81 and stigmastanol is indicted at peak 84. Peaks 65, 66 and 77 in FIG. 2 are co-occurring compounds which may exhibit hypocholesterolemic effects. It is possible, however, that these co-occurring compounds may have a synergistic effect on the actions of the known phytosterols in the compositions. Similarly, in FIGS. 5 and 6, campesterol, stigmastanol and beta-sitosterol are represented at peaks 6, 7 and 8 respectively.

EXAMPLE 1

Extraction and Purification

A batch of 3 kg of pulping soap was obtained from B.C. Chemicals Inc. A mixture of 3 L of acetone and 1.5 L of water was prepared to which the soap was added. The mixture was extracted continuously with 4.5 L of hexane at 50° C. for 24 hours using an 18 L evaporator. The resultant extraction product was then dried over sodium sulphate and allowed to evaporate. This produced 460 g of residue or creamy precipitate.

The creamy precipitate was warmed and stirred using a magnetic bar and 460 ml of methanol was slowly added. The mixture was refluxed under stirring for 15 min. and cooled slowly for 3–5 hours. The mixture was refrigerated at 3°–4° C. overnight and then filtered and washed (twice) with 150 ml cold methanol. Finally, the mixture was maintained in a vacuum for 2 days yielding 100 g of mixture with a purity of 82% (i.e. 82 g of phytosterols).

EXAMPLE 2

Evaluation of the Effects of Phytosterol Compositions in Rats

Ninety male Wistar rats (80–100 g) were divided into 3 experimental modules: Forbes-1 composition; Forbes-2 composition and soybean. The thirty rats within each module were further divided into 5 dietary regimes as indicated in Table 2. The rats were kept on reverse lighting cycle, and fed for 10 days with a basal semi-purified diet (Table 1) supplemented with different amounts of cholesterol and phystosterol (Table 2). Within each of the 5 dietary groups, 2 rats were administered the Forbes-1 composition, 2 rats were administered the Forbes-2 composition and 2 rats were administered soybean-derived phytosterol (Sigma).

TABLE 1

Composition of experimental diet

| Ingredients | % |
| --- | --- |
| Casein | 20 |
| Cornstarch | 21.5 |
| Sucrose | 35 |
| Fixed-oil* | 18 |
| Dl-methionine | 0.5 |
| Mineral mixture | 4.00 |
| Vitamin mixture | 1.00 |

*Safflower and lard mixed in a 1:3 ratio.

TABLE 2

Dietary regimens

| | Sterols added to the basal diet (%) | |
| --- | --- | --- |
| Groups | Cholesterol | Phytosterol |
| 1 | 0 | 0 |
| 2 | 1 | 0 |
| 3 | 1 | 0.2 |
| 4 | 1 | 0.5 |
| 5 | 1 | 1 |

At the end of the feeding period, the rats were intraperitoneally injected with deuterium oxide (0.4 ml) and deprived of food and water for at least 2 hours. The rats were then anaesthetized with halothane. Blood samples were withdrawn from the heart. Samples of liver, small intestine and muscle were quickly removed, weighed, put in liquid nitrogen and stored at 80° C. until determination of cholesterol synthesis. Total cholesterol, LDL and HDL cholesterol were determined with a commercial kit (Biopacific Diagnostic Inc).

Figure 8:
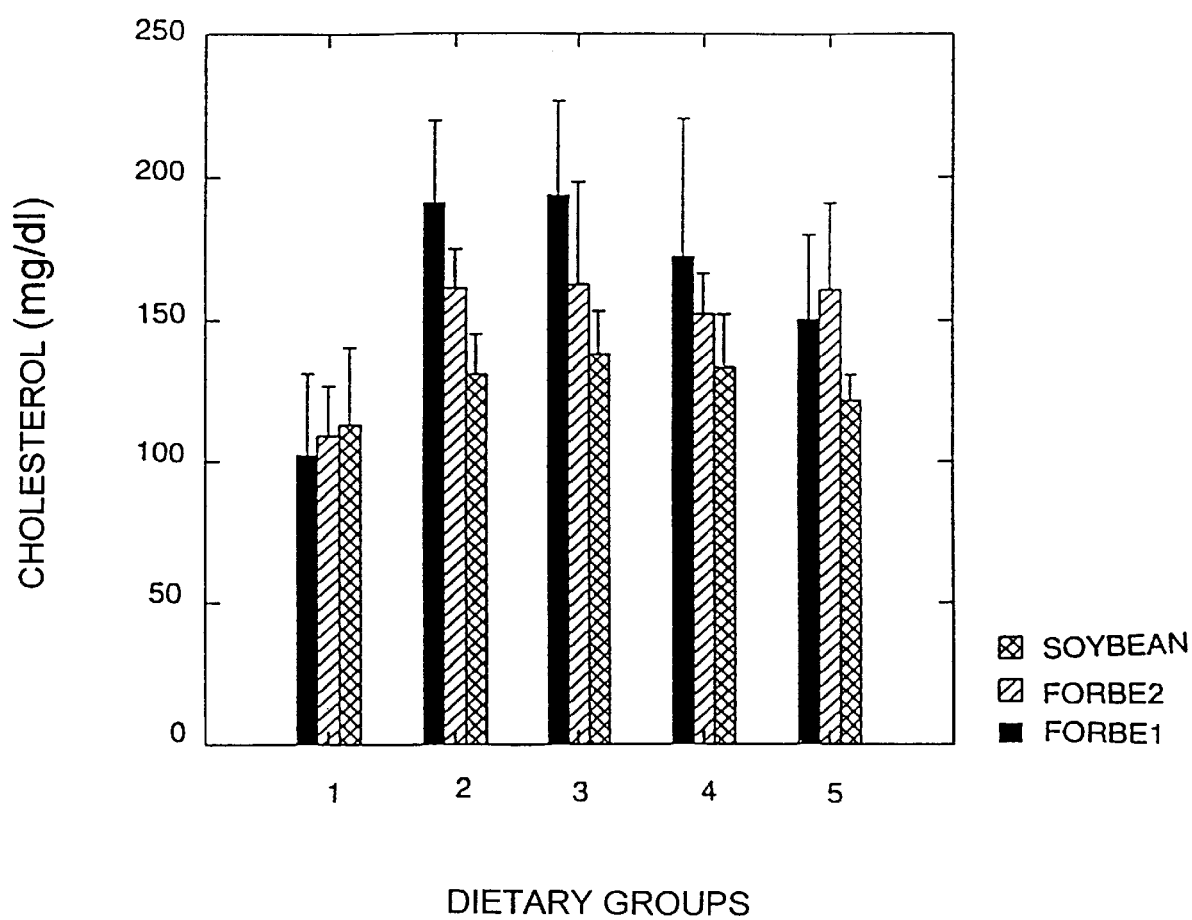
FIG. 8 represents a bar graph illustrating the effects of Forbes-1 and Forbes-2 on TC concentrations in rats.
Figure 9:
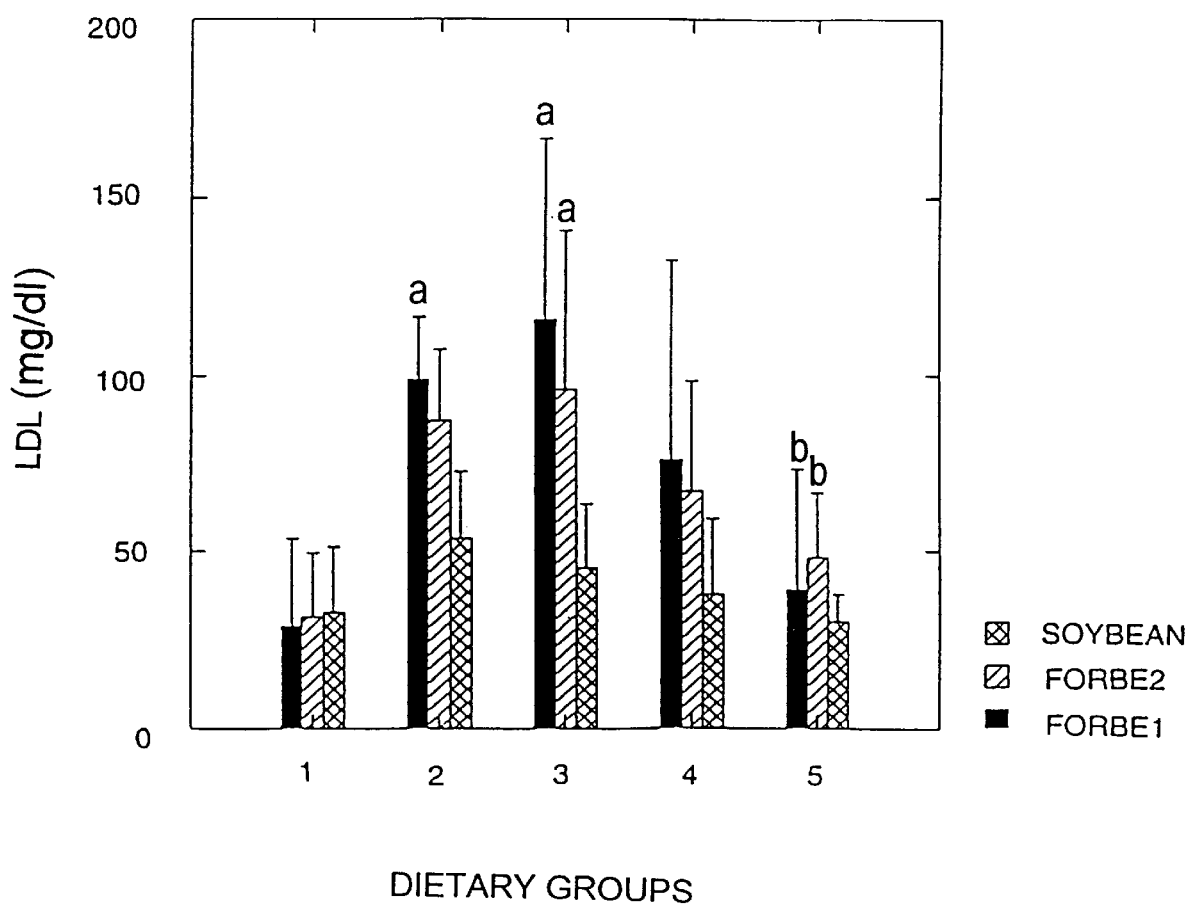
FIG. 9 represents a bar graph illustrating the effects of Forbes-1 and Forbes-2 on LDL-cholesterol concentrations in rats.
Figure 10:
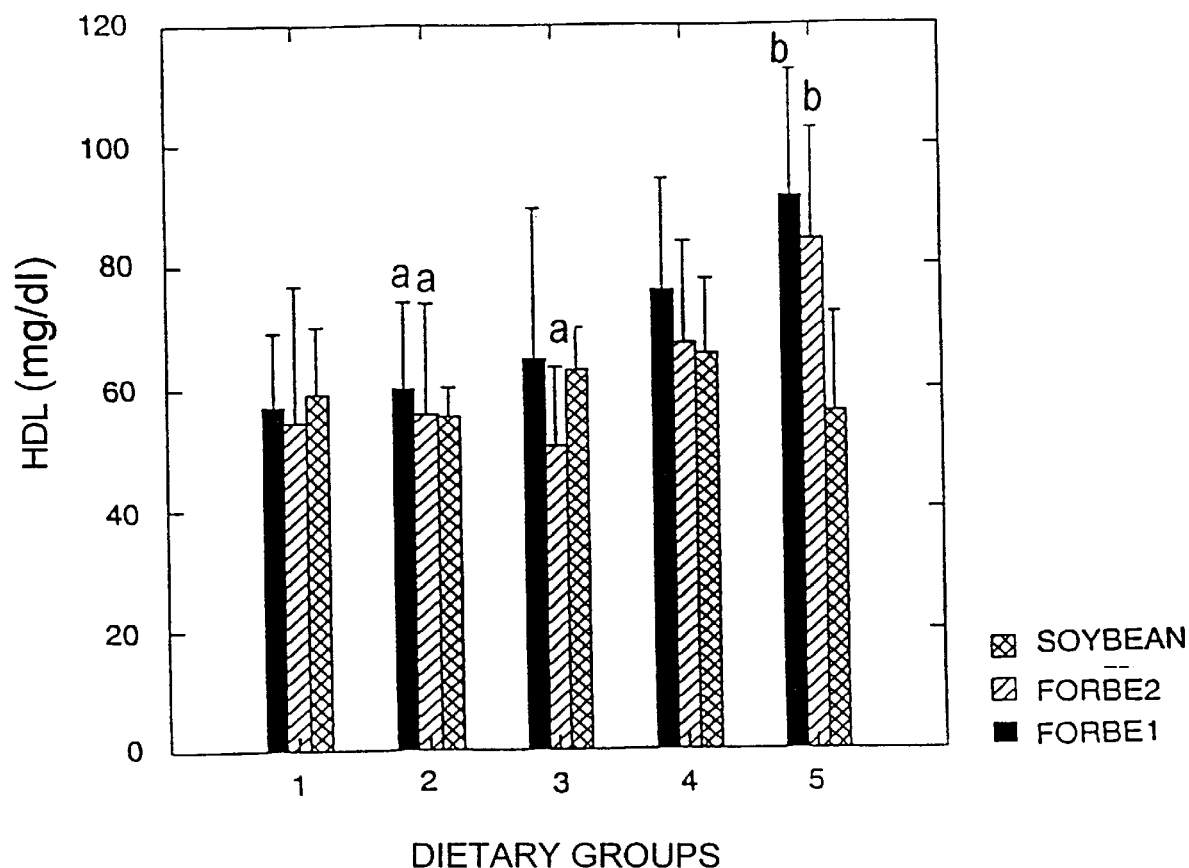
FIG. 10 represents a bar graph illustrating the effects of Forbes-1 and Forbes-2 on HDL-cholesterol concentrations in rats.

The results of the effects of the phytosterol compositions on total cholesterol, LDL and HDL are represented in FIGS. 8, 9 and 10 respectively. The efficacy of the Forbes-1 and Forbes-2 is evident from the reduction in LDL-cholesterol shown in FIG. 9 and in the increase in HDL-cholesterol shown in FIG. 10, particularly by Forbes-1. In FIG. 8, the addition of cholesterol (dietary group 2) to the base diet (group 1) resulted in an increase in circulating cholesterol concentrations. Progressive addition of increasing levels of phytosterols (groups 3–5) resulted in a normalization of cholesterol levels in groups fed Forbes-2 and Forbes-1, but not soybean phytosterols, as determined by regression analysis. FIG. 9 shows that Forbes-2 and Forbes-1 phytosterols possess better cholesterol-lowering efficacy than the soybean phytosterols for LDL. FIG. 10 demonstrates the greater HDL-raising ability of the preferred compositions of the present invention, particularly Forbes-1, compared to the soybean phytosterols.

EXAMPLE 3

Evaluation of Effects of Phytosterol Compositions in Hamsters

The present study was to examine the effect of dietary phytosterol compositions of the present invention on the dietary cholesterol-induced elevation of serum cholesterol concentrations in hamsters.

A total of 40 male hamsters (80–100g), housed individually in stainless mesh cages were fed rodent chow and acclimated for three days in an air conditions room (20°–22° C., lights on 1700–0500). Hamsters were then divided into five groups of 8 animals each group, and fed for 34 days, a basal semi-purified diet (Table 3) supplemented with different amounts of cholesterol and one of the phytosterol compositions of the present invention (Forbes 3) (Table 4).

TABLE 3

Composition of experimental diet

| Ingredients | % by weight |
| --- | --- |
| Casein | 20 |
| Cornstarch | 28 |
| Sucrose | 36.3 |
| Corn oil | 5.0 |
| Cellulose | 5.0 |
| Dl-methionine | 0.5 |
| Mineral mixture | 4.00 |
| Vitamin mixture | 1.00 |
| Choline bitartrate | 0.2 |
| Cholesterol | 0.025, 0.25 |

TABLE 4

| | Dietary regimens | |
|---|---|---|
| Groups | Cholesterol added to control diet % | Phytosterol added to control diet % |
| 1 | 0.025 | None |
| 2 | 0.25 | None |
| 3 | 0.25 | 0.25 |
| 4 | 0.25 | 0.5 |
| 5 | 0.25 | 1.0 |

At the end of the feeding period the animals were intraperitoneally injected with deuterium oxide (0.4 ml), and deprived of food and water for at least 2 hours. The hamsters were then anaesthetized with halothane. Blood samples were withdrawn from the heart. Other tissue samples including liver, small intestine and muscle were quickly removed, weighed, put in liquid nitrogen and stored at −80° C. until determination of cholesterol synthesis. Total cholesterol, HDL and LDL cholesterol were determined using a commercial kit. The results were statistically evaluated with ONEWAY analysis of variance procedure (SYSTAT).

Figure 11:
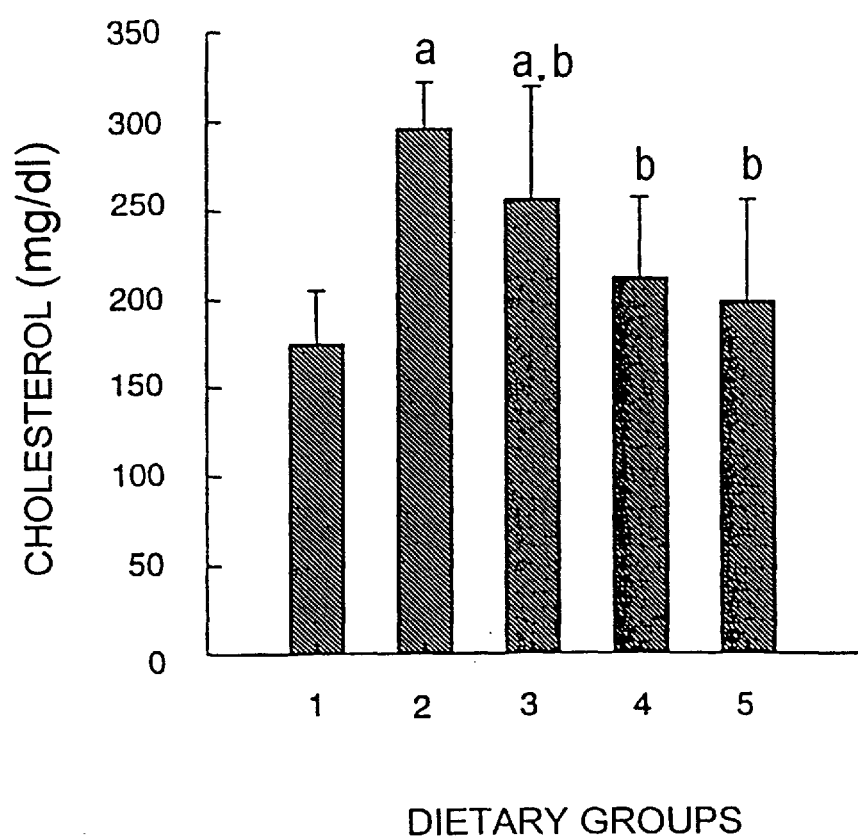
FIG. 11 represents a bar graph illustrating the effects of Forbes-3 on serum TC in hamsters.
Figure 12:
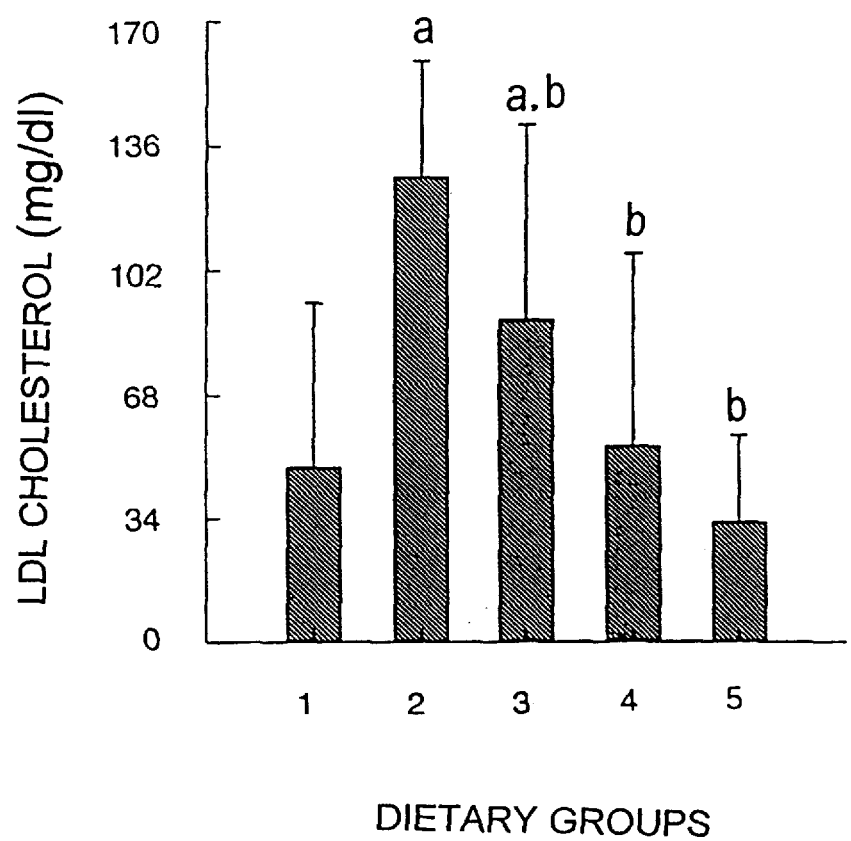
FIG. 12 represents a bar graph illustrating the effects of Forbes-3 on serum LDL-cholesterol in hamsters.

Hamsters fed the high cholesterol diet had significantly higher serum total cholesterol and LDL cholesterol than did those fed the normal cholesterol (0.025%) diet. The supplementation of phytosterol at levels of 0.5% and 1% remarkably abolished these increases induced by high cholesterol consumption (FIGS. 11 and 12). The LDL cholesterol concentration in group 5 was lower compared to the levels in hamsters fed normal cholesterol-containing diets (FIG. 12). Furthermore, there was negative regression association of total cholesterol and LDL cholesterol to the level of phytosterol-added in diet (FIG. 13).

Figure 13:
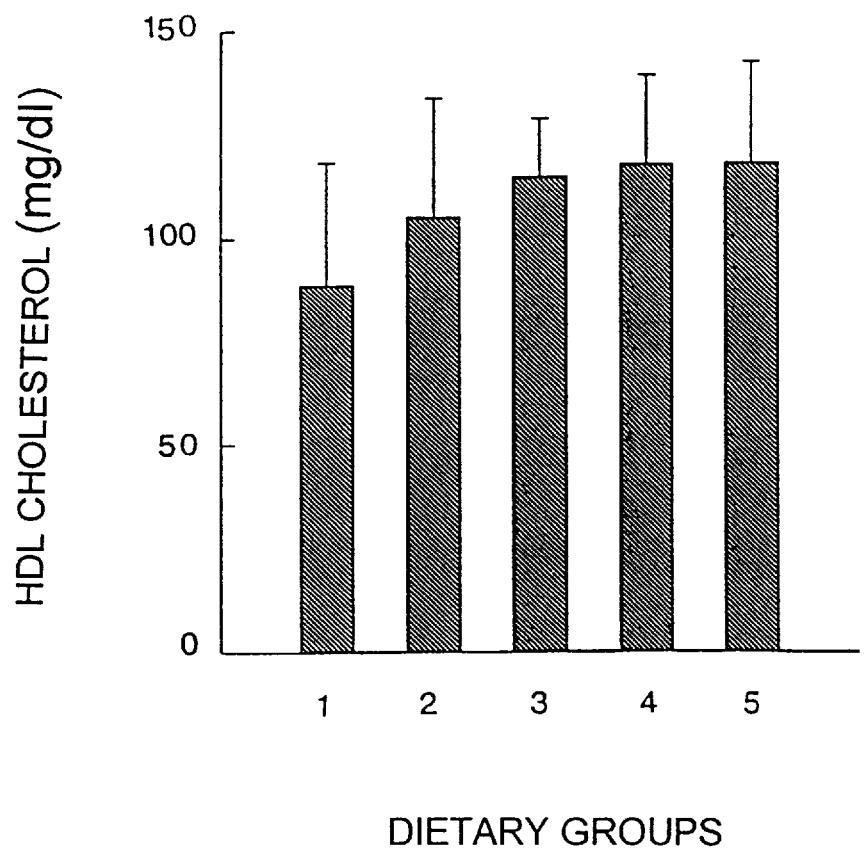
FIG. 13 represents a bar graph illustrating the effects of Forbes-3 on serum HDL-cholesterol in hamsters.

Supplementation of phytosterol caused a slight increase in HDL, but without yielding a significant difference (FIG. 13).

We claim:

1. A process for isolating a phytosterol composition from a pulping soap which comprises:

extracting from the pulping soap a creamy precipitate using a solvent mixture—having no alcohol and —comprising water, ketone and hydrocarbon; and purifying the creamy precipitate to form the phytosterol composition.

2. The process of claim 1 wherein the ketone is 2-propanone.

3. The process of claim 1 wherein the hydrocarbon is selected from the group comprising C5 and C10 hydrocarbons.

4. The process of claim 1 wherein the hydrocarbon is hexane.

5. The process of claim 1 wherein the creamy precipitate is purified by crystallization.

6. A composition prepared according to the process described in claim 1.

* * * * *